US009080780B2

(12) United States Patent
Lee et al.

(10) Patent No.: US 9,080,780 B2
(45) Date of Patent: Jul. 14, 2015

(54) HUMIDIFIER APPARATUS USING A PHOTOCATALYST HAVING AN AIR-CLEANING FUNCTION

(75) Inventors: Ju-Hyung Lee, Uiwang-si (KR); Seong-Moon Jung, Daejeon (KR); Joo-Hwan Seo, Daejeon (KR); Dong-Il Lee, Anyang-si (KR)

(73) Assignee: LG HAUSYS, LTD., Seoul (KR)

( * ) Notice: Subject to any disclaimer, the term of this patent is extended or adjusted under 35 U.S.C. 154(b) by 0 days.

(21) Appl. No.: 13/984,156

(22) PCT Filed: Feb. 28, 2012

(86) PCT No.: PCT/KR2012/001510
§ 371 (c)(1),
(2), (4) Date: Aug. 7, 2013

(87) PCT Pub. No.: WO2012/118329
PCT Pub. Date: Sep. 7, 2012

(65) Prior Publication Data
US 2013/0330238 A1     Dec. 12, 2013

(30) Foreign Application Priority Data

Mar. 2, 2011 (KR) .................... 10-2011-0018413

(51) Int. Cl.
*A61L 9/20* (2006.01)
*F24F 6/12* (2006.01)
(Continued)

(52) U.S. Cl.
CPC . *F24F 6/12* (2013.01); *A61L 9/205* (2013.01); *B01D 53/0407* (2013.01); *B01D 53/885* (2013.01); *F24F 3/1603* (2013.01); *F24F 6/043* (2013.01); *B01D 2253/10* (2013.01); *B01D 2255/20707* (2013.01); *B01D 2255/802* (2013.01); *B01D 2257/708* (2013.01); *B01D 2257/90* (2013.01); *B01D 2257/91* (2013.01);
(Continued)

(58) Field of Classification Search
CPC .................................. A61L 9/04; A61L 9/205
USPC ..................................................... 422/123, 24
See application file for complete search history.

(56) References Cited

U.S. PATENT DOCUMENTS 2,596,801 A * 5/1952 Wilhelmi .......................... 261/97
6,413,303 B2 * 7/2002 Gelderland et al. ............. 96/135
(Continued)

FOREIGN PATENT DOCUMENTS

CN     2522283 Y     11/2002
CN     101590256 A   12/2009
(Continued)

OTHER PUBLICATIONS

Inagaki et al. JP 2008-309439. Dec. 2008. English machine translation from Espacenet.*
(Continued)

*Primary Examiner* — Sean E Conley
*Assistant Examiner* — Donald Spamer
(74) *Attorney, Agent, or Firm* — Lowe Hauptman & Ham, LLP

(57) ABSTRACT

Disclosed is a humidifier apparatus using a photocatalyst having an air-cleaning function, and more particularly, to a humidifier apparatus using a photocatalyst having an air-cleaning function, which is capable of performing an indoor air-cleaning function and a humidifier function while minimizing energy consumption.

16 Claims, 5 Drawing Sheets

(51) Int. Cl.
  *B01D 53/04* (2006.01)
  *B01D 53/88* (2006.01)
  *F24F 3/16* (2006.01)
  *F24F 6/04* (2006.01)
(52) U.S. Cl.
  CPC ... *B01D 2259/4508* (2013.01); *B01D 2259/802* (2013.01); *B01D 2259/804* (2013.01); *F24F 2003/1628* (2013.01)

(56) References Cited

U.S. PATENT DOCUMENTS

| | | | |
|---|---|---|---|
| 2002/0050755 A1 | 5/2002 | Werfel et al. | |
| 2005/0129591 A1 | 6/2005 | Wei et al. | |
| 2007/0221061 A1* | 9/2007 | Steiner et al. | 96/63 |
| 2009/0000325 A1 | 1/2009 | Johnson | |
| 2010/0104470 A1* | 4/2010 | McCabe | 422/22 |

FOREIGN PATENT DOCUMENTS

| | | | | |
|---|---|---|---|---|
| CN | 101590273 | * | 12/2009 | ............ A61L 9/20 |
| JP | 6213946 A | | 1/1987 | |
| JP | 414933 U | | 2/1992 | |
| JP | 09250785 A | | 9/1997 | |
| JP | 2004184058 | | 7/2004 | |
| JP | 2005344979 | | 12/2005 | |
| JP | 2008309439 | | 12/2008 | |
| JP | 2009276034 A | | 11/2009 | |
| KR | 1020010033070 | | 4/2001 | |
| KR | 20-0321269 | | 7/2003 | |
| KR | 20040027002 | | 4/2004 | |
| KR | 100533589 | | 12/2005 | |
| WO | 9305869 | | 4/1993 | |
| WO | 9942764 | | 8/1999 | |
| WO | 2007055430 A1 | | 5/2007 | |

OTHER PUBLICATIONS

Ban et al. CN 101590273. Dec. 2009. English machine translation from Espacenet.*
International Search Report mailed Sep. 25, 2012 for PCT/KR2012/001510.
Japanese Office Action dated Jun. 10, 2014.
Japanese Notice of Allowance dated Feb. 3, 2015.
Chinese Office Action dated May 6, 2015.

* cited by examiner

[Fig. 1]
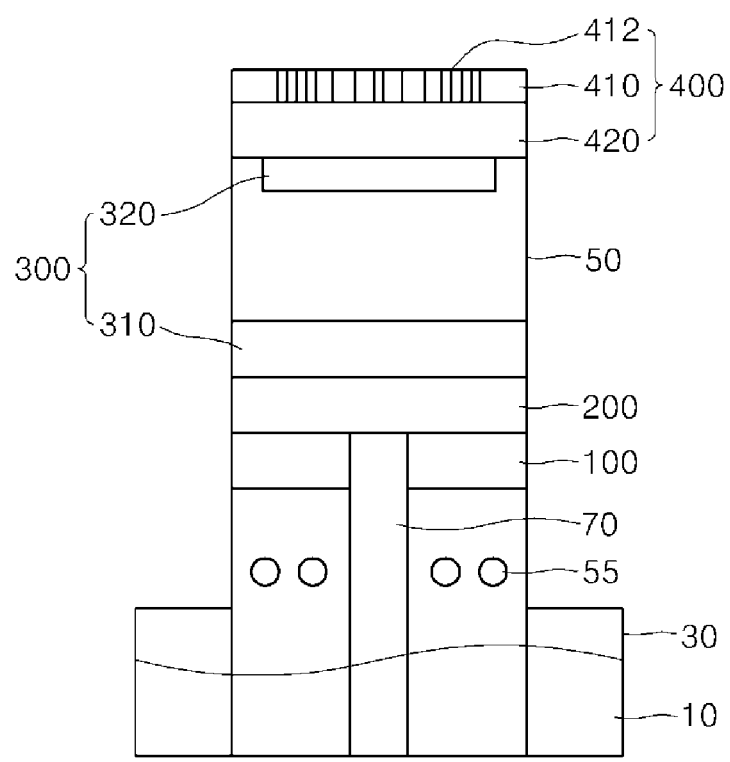

[Fig. 2]
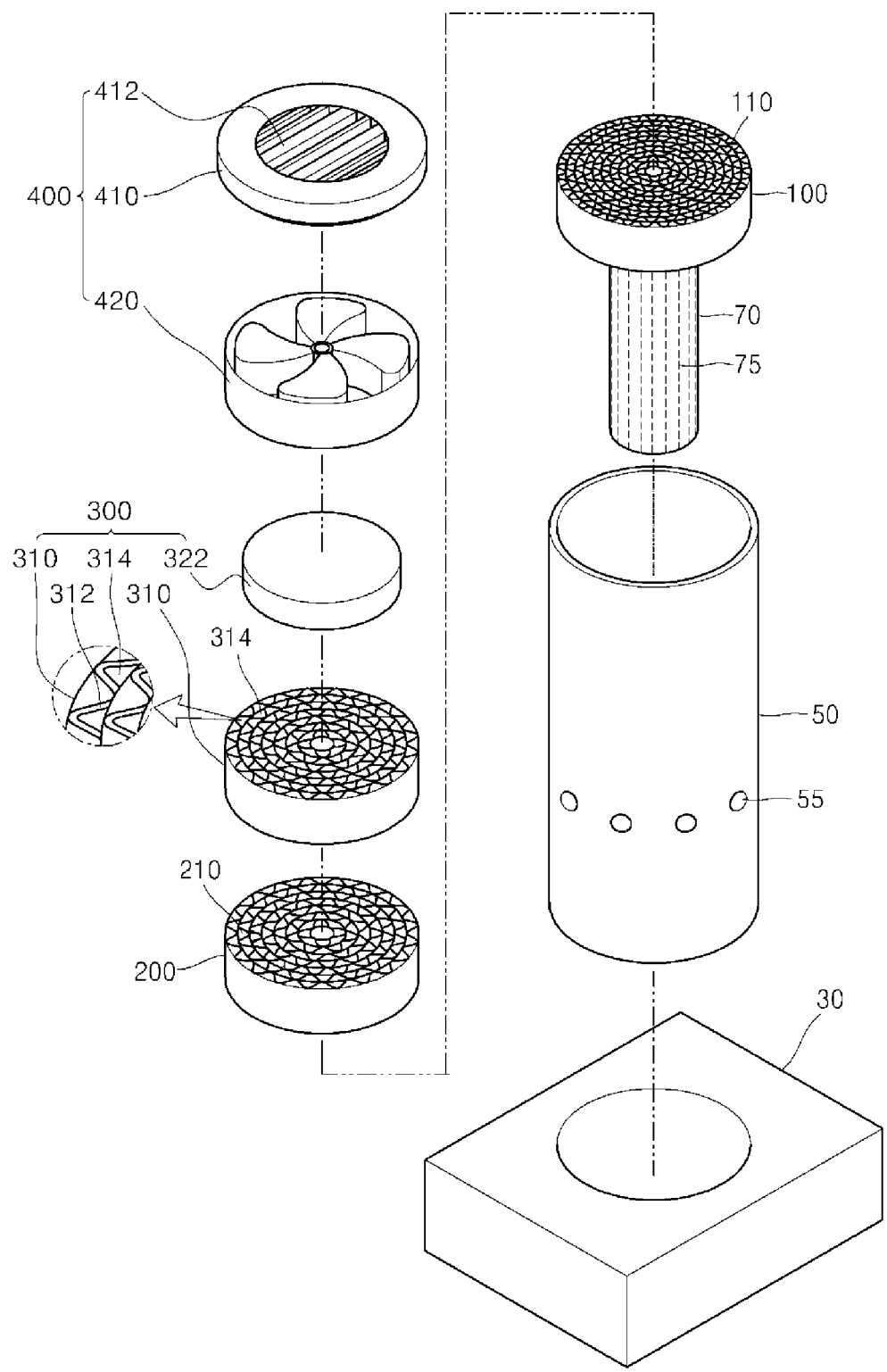

[Fig. 3]
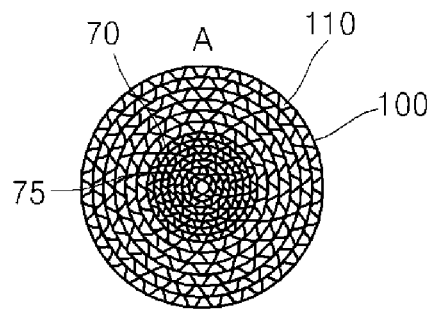
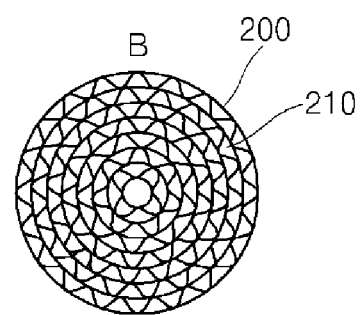
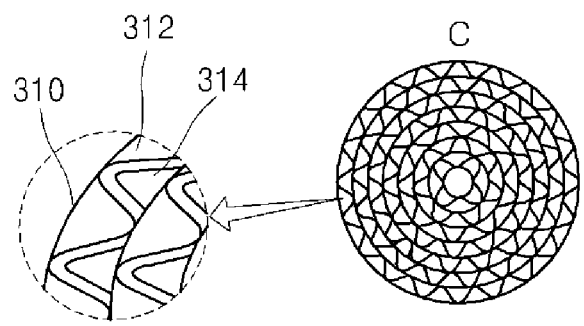

[Fig. 4]
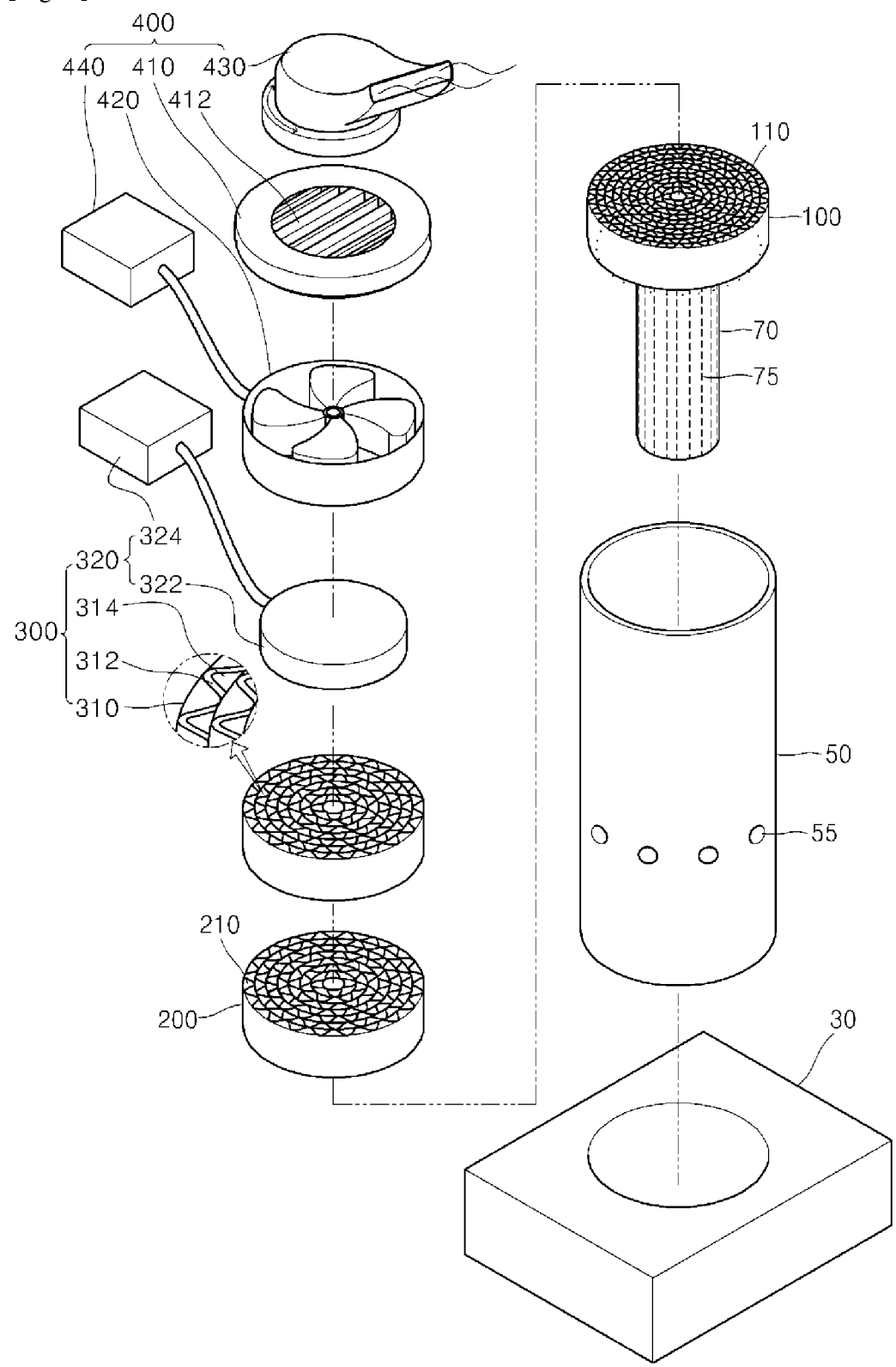

[Fig. 5]
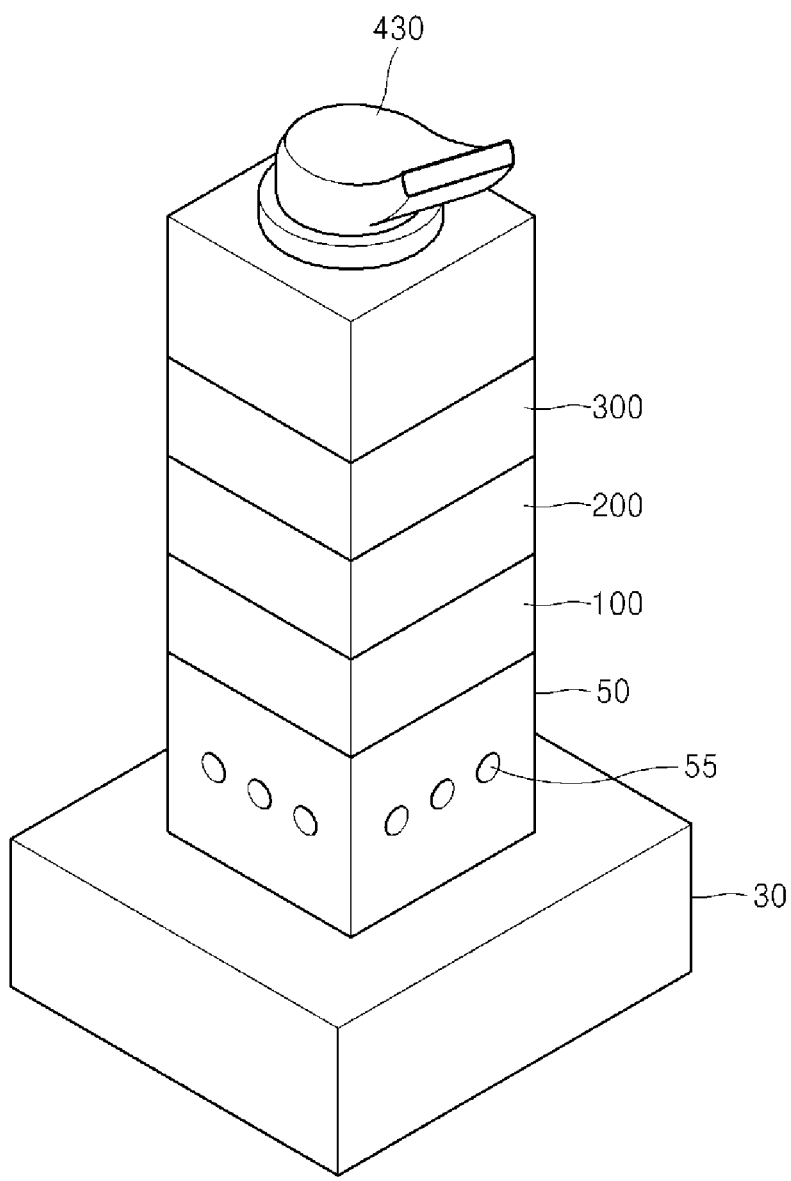

HUMIDIFIER APPARATUS USING A PHOTOCATALYST HAVING AN AIR-CLEANING FUNCTION

CROSS REFERENCE TO RELATED APPLICATION

This application claims the priority of Korean Patent Application No. 10-2011-0018413, filed on Mar. 2, 2011 in the KIPO (Korean Intellectual Property Office). Further, this application is the National Phase application of International Application No. PCT/KR2012/001510 filed on Feb. 28, 2012, which designates the United States and was published in Korean.

TECHNICAL FIELD

The present invention relates to a humidifier apparatus using a photocatalyst having an air-cleaning function, and more particularly, to a humidifier apparatus using a photocatalyst, which can provide an air-cleaning function and a humidification function while minimizing energy consumption.

BACKGROUND ART

Currently, most people spend 90% of the day in a room and are exposed to a variety of gaseous contaminants, such as volatile organic compounds, radon, and microorganisms.

Thus, it is very important to supply clean air into a room through purification of indoor air.

Accordingly, the interior of a house, office, school, or the like is generally provided with an air cleaner for purification of indoor air.

In addition, although an air cleaner and a humidifier have been manufactured as separate products, a product combining an air-cleaning function and a humidification function has recently been introduced to the market to satisfy consumer demand.

Conventionally, an anion generating type system is used to provide moisture while purifying indoor air.

However, the anion generating type system adopts electrolysis by generating a spark upon application of high voltage to metallic electrode rods, and thus has problems such as anion emission and generation of activated oxygen and ozone.

In addition, anion generating efficiency can be significantly reduced when dust or foreign matter is attached to a surface of a discharge plate.

Further, a system of generating anions through decomposition of water into fine droplets through centrifugation has a complicated structure and produces severe motor noise.

DISCLOSURE

Technical Problem

An aspect of the present invention is to provide a humidifier apparatus using a photocatalyst having an air-cleaning function, which can provide moisture while purifying indoor air and can be semi-permanently used using a photocatalyst.

Another aspect of the present invention is to provide a humidifier apparatus using a photocatalyst having an air-cleaning function, which permits easy installation and disassembly and can reduce energy consumption in use.

A further aspect of the present invention is to provide a humidifier apparatus using a photocatalyst having an air-cleaning function, which does not generate noise in use while improving indoor environment.

Yet another aspect of the present invention is to provide a humidifier apparatus using a photocatalyst having an air-cleaning function, which includes a column type housing to permit optimal utilization of space per unit area and filter pores disposed inside the apparatus and each having a close and dense honeycomb shape.

Technical Solution

In accordance with one aspect of the present invention, a humidifier apparatus using a photocatalyst having an air-cleaning function includes:

a housing, which has a lower portion being received in a water tank for storing water, and includes an inlet hole for intake of external air into the housing; an absorption bar being disposed within the housing so as to allow a lower portion of the absorption bar to be submerged in the water, which includes a plurality of adsorption pores combined to absorb the water; a humidifying filter being secured to an inner surface of the housing and covering an upper portion of the absorption bar, which includes a plurality of humidifying pores combined with each other; an adsorption filter being stacked on the humidifying filter, which includes a plurality of adsorption pores combined with each other to adsorb foreign matter introduced into the housing; a photocatalyst cleaning unit being stacked on the adsorption filter, which purges the foreign matter adsorbed to the adsorption filter; and a discharge unit being disposed above the photocatalyst cleaning unit, which absorbs the moisture supplied from the humidifying filter and air from the housing, and discharges the absorbed moisture and air to an outside of the housing.

The photocatalyst cleaning unit may include a photocatalyst filter being stacked on the adsorption filter, which includes a plurality of photocatalyst pores coated with a photocatalyst and combined in a honeycomb shape so as to purge the foreign matter adsorbed to the adsorption filter; and a light supply unit being disposed above the photocatalyst filter, which emits light to the photocatalyst included in the photocatalyst filter to activate the photocatalyst.

The light supply unit may include a light emitting unit, which comprises a light emitting diode (LED); and a power controller controlling the light emitting unit to be operated by alternating power and controlling the light emitting unit to be turned on/off.

The discharge unit may include a discharge plate, which covers an upper portion of the housing, and includes a plurality of through-holes formed therein; and a discharge fan being disposed under the discharge plate, which suctions air from the housing, and discharges the air through the discharge plate.

The discharge unit may further include a guide piece being connected to an upper portion of the discharge plate, which guides flow of the air discharged through the through-holes.

The discharge unit may further include a discharge controller, which regulates an amount of air discharged from the housing to the outside by outside controlling the discharge fan.

The housing may have a cylindrical shape.

The inlet hole may be formed at a location of the housing below the humidifying filter and above the water.

Advantageous Effects

The humidifier apparatus according to the present invention a photocatalyst with a semi-permanent lifespan and thus has high energy efficiency, thereby providing economic feasibility through reduction in operating costs.

The humidifier apparatus according to the present invention can supply moisture into a dry room while purifying indoor air, and facilitates installation and disassembly thereof.

The humidifier apparatus according to the present invention does not generate noise in use while maintaining a humidification function and an air-cleaning function.

The humidifier apparatus according to the present invention has a column type outer appearance and includes filters arranged within the housing and including pores closely and densely combined in a honeycomb shape, thereby enabling efficient utilization of space per unit area.

DESCRIPTION OF DRAWINGS

FIG. 1 is a diagram of a humidifier apparatus using a photocatalyst having an air-cleaning function in accordance with the present invention.

FIG. 2 is an exploded perspective view of the humidifier apparatus using a photocatalyst having an air-cleaning function in accordance with the present invention.

FIG. 3 shows cross-sectional views of main parts of the humidifier apparatus using a photocatalyst having an air-cleaning function in accordance with the present invention.

FIG. 4 is an exploded perspective view of a humidifier apparatus using a photocatalyst having an air-cleaning function in accordance with one embodiment of the present invention.

FIG. 5 is an exploded perspective view of a humidifier apparatus using a photocatalyst having an air-cleaning function in accordance with another embodiment of the present invention.

BEST MODE

In the following detailed description of various specific embodiments in which the present invention may be practiced, reference is made to the accompanying drawings by way of illustration. These embodiments will be described so as to provide thorough understanding of the present invention such that the present invention can be practiced by those skilled in the art. It should be understood that the various embodiments of the invention, although different, are not necessarily mutually exclusive. For example, particular features, structures or characteristics described in one embodiment may be included in other embodiments without departing from the spirit and scope of the present invention. Furthermore, it should be understood that embodiments of the invention may be implemented using different technologies. Further, it should be understood that locations or arrangements of individual components in the respective embodiments can be changed without departing from the spirit and scope of the present invention. The following detailed description is, therefore, not to be taken in a limiting sense, and the scope of the present invention is defined only by the appended claims, along with the full scope of equivalents to which such claims are entitled. In the drawings, like reference numerals denote the same or similar components throughout several aspects, and areas, thicknesses, shapes and the like can be exaggerated for convenience in description.

Now, exemplary embodiments of the present invention will be described in detail with reference to the accompanying drawings so as to allow the present invention to be easily practiced by those skilled in the art to which the present invention pertains.

Here, it should be understood that the technical features of a humidifier apparatus using a photocatalyst having an air-cleaning function according to the present invention, particularly, the technical features of a humidifying filter and a photocatalyst filter, may be applied to other fields directed to, for example, providing an air-cleaning function and a humidification function while minimizing energy consumption.

FIG. 1 is a diagram of a humidifier apparatus using a photocatalyst having an air-cleaning function in accordance with the present invention.

Referring to FIG. 1, a housing 50 and components in the housing 50 will be described. The housing 50 has a cylindrical shape and is placed upright Humidification refers to supply of moisture to a room in a dry condition and requires supply of water 10.

For humidification, the humidifier apparatus according to the invention is provided with a water tank 30 which stores the water 10.

The housing 50 is placed in the apparatus such that a lower portion of the housing is accommodated in the water tank 30.

In addition, the housing 50 is formed with a plurality of inlet holes 55 through which external air can be introduced into the housing 50.

Here, the inlet holes 55 are formed at a location above the water 10 so as to prevent interference with the water 10.

Further, the housing 50 is provided therein with an absorption bar 70, which has a lower portion extending into the water 10 and includes a plurality of absorption pores 75 combined in a bar or cylindrical shape so as to absorb the water.

The absorption bar 70 serves to absorb the water 10 through the plurality of the absorption pores 75.

Here, the absorption bar 70 is provided with a humidifying filter 100 configured to surround an upper portion of the absorption bar 70.

The humidifying filter 100 includes a plurality of humidifying pores 110 combined in a honeycomb shape and closely secured to an inner surface of the housing 50.

The humidifying filter 100 serves to absorb the water 10 from the absorption bar 70.

As such, the humidifying filter 100 provides a humidification function by allowing the water absorbed from the absorption bar 70 to evaporate.

Preferably, the humidifying filter 100 is placed on a holder (not shown), which is formed on the inner surface of the housing 50 to hold the humidifying filter 100.

Preferably, the holder protrudes from the inner surface of the housing 50 in a horizontal direction and is configured so as not to obstruct the function of the absorption bar 70 and the function of the humidifying filter 100 receiving the water 10 through the absorption bar 70.

As such, in the apparatus, the water 10 is absorbed into the humidifying filter 100 through the absorption bar 70 and evaporated from the humidifying filter 100, thereby providing moisture to a room.

An adsorption filter 200 shaped corresponding to the humidifying filter 100 is placed on the humidifying filter 100.

The adsorption filter 200 is stacked on the humidifying filter 100 and includes a plurality of adsorption pores 210 combined in a honeycomb shape to adsorb dust or contaminants introduced into the housing 50.

In addition, a photocatalyst cleaning unit 300 is placed on the adsorption filter 200.

The photocatalyst cleaning unit 300 serves to purge the contaminants adsorbed to the adsorption filter 200.

The photocatalyst cleaning unit 300 is shaped corresponding to the adsorption filter 200 and is stacked on the adsorption filter 200. The photocatalyst cleaning unit 300 is provided with a photocatalyst filter 310, which includes a plurality of photocatalyst pores 314 coated with a photocatalyst 312 and combined in a honeycomb shape.

Further, the photocatalyst cleaning unit 300 includes a light supply unit 320 placed above the photocatalyst filter 310 and emitting light to the photocatalyst 312 in the photocatalyst filter 310 to activate the photocatalyst 312.

Further, the apparatus includes a discharge unit 400 placed above the photocatalyst cleaning unit 300.

The discharge unit 400 is placed above the photocatalyst cleaning unit 300 and suctions the moisture supplied from the humidifying filter 100 and air from the housing 50 to discharge the moisture and air to the outside of the housing 50.

Here, the discharge unit 400 includes a discharge plate 410, which is configured to cover an upper portion of the housing 50 and formed with a plurality of through-holes 412.

Further, the discharge unit 400 includes a discharge fan 420, which is disposed under the discharge plate 410 and suctions air from the housing 50 to discharge the air to the outside through the discharge plate 410.

As such, when air containing contaminants enters the housing 50, the contaminants are adsorbed to the adsorption filter 200 and purged through the photocatalyst cleaning unit 300 to provide purified air, which in turn is discharged to the outside of the housing 50 through the discharge unit 400.

FIG. 2 is an exploded perspective view of the humidifier apparatus using a photocatalyst having an air-cleaning function in accordance with the present invention.

Referring to FIG. 2, the components of the humidifier apparatus shown in FIG. 1 are dissembled. Now, these components will be described in more detail.

The water tank 30 stores water 10, and the housing 50 having a cylindrical shape stands upright and has a lower portion extending into the water 10.

The housing 50 receives the absorption bar 70, which includes the plurality of absorption pores 75 combined in a bar shape.

Here, the absorption bar 70 has a lower portion received in the water 10.

With this configuration, the absorption pores 75 of the absorption bar 70 efficiently absorb water 10 through capillary action, whereby the entirety of the absorption bar 70 can absorb the water 10.

In addition, the absorption bar 70 is connected at the upper portion thereof to the humidifying filter 100.

The humidifying filter 100 is connected to the upper portion of the absorption bar 70 to surround an outer periphery of the upper portion of the absorption bar 70, includes the plurality of humidifying pores 110 combined in a honeycomb shape, and is closely secured to the inner surface of the housing 50.

The humidifying pores 110 are in close contact with each other to achieve efficient absorption of the water 10 from the absorption bar 70 and are arranged along the circular inner surface of the housing 50 to constitute the humidifying filter 100.

In particular, the housing 50 is formed with inlet holes 55 through which external air can be introduced into the housing 50.

Such inlet holes 55 are formed at a location of the housing above an upper level of the water 10 contained in the water tank 30 and below a lower side of the humidifying filter 100.

That is, the location of the inlet holes 55 is determined so as to allow air introduced into the housing 50 through the inlet holes 55 to supply moisture to a room while evaporating the water suctioned into the humidifying filter 100.

The adsorption filter 200 is placed on the humidifying filter 100.

The adsorption filter 200 has a shape corresponding to the shape of the humidifying filter 100, includes the plurality of adsorption pores 210 combined in a honeycomb shape, and is closely secured to the inner surface of the housing 50.

That is, the adsorption pores 210 are in close contact with each other to achieve efficient adsorption of contaminants in air introduced into the housing 50 through the inlet holes 55 and are arranged along the circular inner surface of the housing 50 to constitute the adsorption filter 100.

As a result, in the adsorption filter 200, the plural adsorption pores 210 are combined in a honeycomb shape and efficiently adsorb contaminants such as volatile organic compounds (VOCs) from air introduced into the housing 50.

With such a configuration, contaminants adsorbed to the adsorption filter 200 are purged through the photocatalyst cleaning unit 300 on the adsorption filter 200, so that purified air can be finally supplied from the photocatalyst cleaning unit 300.

In particular, the housing 50 is formed in a column shape and both the humidifying pores 110 of the humidifying filter 100 and the adsorption pores 210 of the adsorption filter 200 are formed in a honeycomb structure, thereby improving space utilization per unit area.

Further, when the humidifying pores 110 or the adsorption pores 210 have a circular cross-section, a space can be created at a portion other than portions where circles meet each other, even in the case where the plural humidifying pores 110 or adsorption pores 210 are in close contact with each other.

In the present invention, each of the humidifying pores 110 and the adsorption pores 210 has a honeycomb-shaped cross-section, for example, a hexagonal structure.

With such a honeycomb-shaped hexagonal cross-section, each of the humidifying pores 110 or each of the adsorption pores 210 can be in close contact with other hexagonal humidifying or adsorption pores without creating a space between the pores.

Accordingly, the humidifying pores 110 or the adsorption pores 210 having a honeycomb-shaped hexagonal cross-section can be brought into close and dense contact with each other without creating a space therebetween.

Further, the humidifying pores 110 of the humidifying filter 100 and the adsorption pores 210 of the adsorption filter 200 are combined in a honeycomb structure and disposed in a close and dense arrangement, thereby providing optimal space utilization.

Further, the photocatalyst cleaning unit 300 includes a photocatalyst filter 310 stacked on the adsorption filter 200, and a light supply unit 320 stacked above the photocatalyst filter 310.

The plural photocatalyst pores 314 coated with the photocatalyst 312 are brought into close contact with each other and combined in a honeycomb shape so as to allow contaminants adsorbed to the adsorption filter 200 to be efficiently purged, and are arranged along the circular inner surface of the housing 50, thereby constituting the photocatalyst filter 310.

Here, the plurality of photocatalyst pores 314 is formed to receive a large amount of the photocatalyst 312 in a narrow space.

The light supply unit 320 emits light to the photocatalyst 312 coated on the photocatalyst filter 310 to activate the photocatalyst 312.

The light supply unit 320 may include a light emitting unit 322, which is constituted by a light emitting diode (LED).

Here, it should be understood that the LED of the light emitting unit 322 is illustrated as one embodiment and the light emitting unit 322 may include a variety of lamps (not shown) as needed.

In particular, the light emitting unit 322 may emit visible or UV (ultraviolet) light through a separate lamp capable of emitting both visible and UV light.

As such, the light emitting unit 322 may emit UV or visible light.

In particular, the photocatalyst 312 refers to a material which can receive light to promote chemical reaction, and such reaction can be called a photochemical reaction.

Here, the photocatalyst 312 may employ a visible light catalyst which can be activated to promote reaction by visible light, or a UV light catalyst (titanium dioxide ($TiO_2$) which can be activated to promote the reaction by UV light according to the kind of light emitted from the LED. The photocatalyst 312 serves to decompose contaminants including a toxic substance within the housing 50 while providing an antibacterial function and an anti-fouling function.

Further, the discharge unit 400 is place on the photocatalyst cleaning unit 300.

The discharge unit 400 includes the discharge plate 410, which is configured to cover the upper portion of the housing 50 and formed with the plurality of through-holes 412.

Further, the discharge unit 400 includes the discharge fan 420 disposed under the discharge plate 410 to suction air from the housing 50 and discharge the air to the outside through the discharge plate 410.

The discharge plate 410 allows only purged moisture to be discharged to the outside of the housing 50 through the through-holes 412 of the discharge plate 410. Here, moisture evaporated from the humidifying filter 100 is purged while passing through the adsorption filter 200 and the photocatalyst cleaning unit 300.

The discharge fan 420 allows the purged moisture to be more efficiently discharged through the discharge plate 410.

FIG. 3 shows cross-sectional views of main parts of the humidifier apparatus using a photocatalyst having an air-cleaning function in accordance with the present invention.

In FIG. 3, a cross-sectional view A of the absorption bar 70 including the absorption pores 75 and the humidifying filter 100 including the humidifying pores 110 is shown.

In addition, a cross-sectional view B of the adsorption filter 200 including the adsorption pores 210 is shown.

Further, a cross-sectional view C of the photocatalyst filter 310 including the photocatalyst 312 and the photocatalyst pores 314 is shown.

Referring to the cross-sectional view A, the plurality of absorption pores 75 is combined to have a circular cross-section so as to absorb water.

In addition, in the humidifying filter 100 surrounding part of the absorption bar 70, the plurality of humidifying pores 110 is combined to have a circular cross-section.

Here, the absorption pores 75 may have a diameter of 1 μm to 20 μm.

If the diameter of the absorption pores 75 exceeds 20 μm, the adsorption pores can provide insufficient capillary action, thereby reducing the amount of water suctioned into the absorption pores 75.

Further, the humidifying pores 110 may have a diameter of 20 μm to 35 μm.

If the diameter of the humidifying pores 110 is less than 20 μm, a humidifying media can suffer from rapid reduction in lifespan due to deposition of inorganic ions in water.

If the diameter of the humidifying pores 110 exceeds 35 μm, the humidifying filter 100 is unlikely to absorb water and thus cannot function properly.

In addition, the absorption bar 70 and the humidifying filter 100 may be formed of glass fibers, pulps, or titanium dioxide ($TiO_2$).

Referring to the cross-sectional view B, a cross-section of the adsorption filter 200 including the adsorption pores 210 is shown.

Here, in the adsorption filter 200, the plurality of the adsorption pores 210 is combined to have a circular cross-section.

In addition, the adsorption filter 200 including the plurality of the adsorption pores 210 serves to adsorb moisture introduced into the housing 50.

Here, the adsorption filter 200 employs an adsorbent, and the plurality of adsorption pores 210 is provided to increase an adsorption area of the contaminants with respect to the adsorbent.

The adsorbent may be selected from among activated carbon, diatomite, zeolite, silica gel, starch, bentonite, alumina, and the like.

Referring to the cross-sectional view C, a cross-section of the photocatalyst filter 310 including the photocatalyst pores 314 is shown.

Here, in the photocatalyst filter 310, the plurality of the photocatalyst pores 314 is combined to have a circular cross-section.

In addition, the photocatalyst 312 is spray-coated on the surfaces of the photocatalyst pores 314.

Here, provided a UV light source, the photocatalyst 312 may be formed of titanium dioxide ($TiO_2$), and provided a visible light source, the photocatalyst 312 may be formed of $TiO_2$ or a visible light catalyst loaded with a noble metal, such as Pt, Au, Ag, and the like. The photocatalyst 312 serves to decompose contaminants including toxic substances within the housing 50 through oxidation while providing an antibacterial function and an anti-fouling function.

The photocatalyst 312 promotes chemical reaction upon receiving light. Thus, the photocatalyst is further activated through photochemical reaction when exposed to light in UV or visible light wavelength bands.

FIG. 4 is an exploded perspective view of a humidifier apparatus using a photocatalyst having an air-cleaning function in accordance with one embodiment of the present invention.

Referring to FIG. 4, other components are added to the humidifier apparatus shown in FIG. 2.

A housing 50 having a cylindrical shape is provided with inlet holes 55, through which external air is introduced into the housing 50, and has a lower portion submerged in water 10 which fills a water tank 30.

The housing 50 is provided with an absorption bar 70, which includes a plurality of absorption pores 75 combined to absorb the water 10 through capillary action.

Further, a humidifying filter 100 is connected to an upper portion of the absorption bar 70 to surround an outer periphery of the upper portion of the absorption bar 70 and includes a plurality of humidifying pores 110 combined in a honeycomb shape. The humidifying filter 100 is closely secured to an inner surface of the housing 50.

Such a humidifying filter 100 absorbs the water 10 through the absorption bar 70 and supplies moisture into a room while evaporating the water 10.

Further, an adsorption filter 200 having a shape corresponding to the humidifying filter 100 is stacked on the humidifying filter 100.

The adsorption filter 200 also includes a plurality of adsorption pores 210 combined in a honeycomb shape and is closely secured to the inner surface of the housing 50.

The adsorption pores 210 serve to adsorb contaminants in air introduced into the housing through the inlet holes 55.

Here, the adsorption filter 200 employs an adsorbent.

The plurality of adsorption pores 210 is provided to increase an adsorption area of contaminants with respect to the adsorbent.

As such, in the adsorption filter 200, the plurality of adsorption pores 210 combined in a honeycomb shape has a function of efficiently adsorbing dust or contaminants introduced into the housing 50.

Further, the contaminants adsorbed to the adsorption filter 200 are decomposed by the photocatalyst cleaning unit 300.

Here, the photocatalyst cleaning unit 300 includes a photocatalyst filter 310 stacked on the adsorption filter 200, and a light supply unit 320 stacked above the photocatalyst filter 310

The photocatalyst filter 310 includes the plurality of the photocatalyst pores 314 combined to have a circular shape.

Further, the photocatalyst pores 314 are coated with the photocatalyst 312 by spraying the photocatalyst 312 onto the surfaces of the photocatalyst pores 314.

As such, contaminants adsorbed to the adsorption filter 200 can be efficiently decomposed through the photocatalyst filter 310 in which the plurality of photocatalyst pores 314 coated with the photocatalyst 312 is combined.

The light supply unit 320 includes a light emitting unit 322, which is constituted by a light emitting diode (LED).

As described above, the light emitting unit 322 may emit UV light through a variety of lamps, as needed.

Further, the light supply unit 320 includes a power controller 324 which controls the light emitting unit 322 to be operated by alternating power and controls the light emitting unit 322 to be turned on/off.

The power controller 324 controls the intensity of light emitted from the light emitting unit 322 to the photocatalyst filter 310 to regulate activation of the photocatalyst 312 in the photocatalyst filter 310.

As such, the contaminants adsorbed to the adsorption filter 200 can be efficiently decomposed in the photocatalyst filter 310 by controlling the light emitting unit 322 through the power controller 324.

Further, the light emitting unit 322 emits light in UV and visible wavelength bands to activate the photocatalyst 312.

Here, the photocatalyst 312 may be composed of titanium dioxide ($TiO_2$) and serve to decompose the contaminants in the housing 50 through oxidation while providing an anti-bacterial function and an anti-fouling function.

In addition, a discharge unit 400 is stacked on the photocatalyst cleaning unit 300.

The discharge unit 400 includes a discharge plate 410, which is configured to cover an upper portion of the housing 50 and formed with a plurality of through-holes 412.

Further, the discharge unit 400 includes a discharge fan 420 disposed under the discharge plate 410 to suction air from the housing 50 and discharge the air to the outside through the discharge plate 410.

The discharge unit 400 further includes a guide piece 430 connected to an upper portion of the discharge plate 410 to guide flow of the air discharged through the through-holes 412.

Upon discharge of air to the outside from the housing 50, the guide piece 430 guides the flow of the air while rotating in a state of being coupled to the upper portion of the discharge plate 410.

In particular, the discharge unit 400 further includes a discharge controller 440 placed outside and controlling the discharge fan 420 to regulate the amount of air discharged from the housing 50 to the outside.

The discharge controller 440 controls the rotating speed of the discharge fan 420 to control the amount of air discharged from the housing 50 to the outside.

FIG. 5 is an exploded perspective view of a humidifier apparatus using a photocatalyst having an air-cleaning function in accordance with another embodiment of the present invention.

In FIG. 5, the humidifier apparatus according to this embodiment includes a housing 50 having a different structure from the above embodiment.

The housing 50 may have a square pillar shape.

Further, the housing 50 has a lower portion partially received in a water tank 30 which stores water 10.

Here, the housing 50 is formed with a plurality of inlet holes 55 through which external air can be introduced into the housing 50, in which the inlet holes are formed at a location of the housing between an upper level of the water 10 in the water tank 30 and a humidifying filter 100.

The humidifying filter 100 has a shape corresponding to an inner surface of the housing 50 and is brought into close contact therewith.

Here, the humidifying filter 100 serves to absorb the water 10 in order to supply moisture into a room.

Likewise, an adsorption filter 200 having a shape corresponding to the humidifying filter 100 is stacked on the humidifying filter 100.

Here, the adsorption filter 200 serves to adsorb contaminants such as dust in air introduced into the housing 50 through the inlet holes 55.

Further, a photocatalyst cleaning unit 300 is placed on the adsorption filter 200 to purge the contaminants adsorbed to the adsorption filter 200.

Such a photocatalyst cleaning unit 300 serves to supply purified air into a room through the housing 50 by purging the contaminants adsorbed to the adsorption filter 200.

In addition, air purified by the photocatalyst cleaning unit 300 is discharged from the housing 50 through the guide piece 430.

Here, since the guide piece 430 can be rotated while being coupled to an upper portion of the housing 50, it is possible to discharge the air from the housing 50 in various directions as needed.

Although not shown in FIG. 5, the housing 50 may have other shapes, for example, a polygonal pillar shape. In this case, it is desirable that the humidifying filter 100, the adsorption filter 200 and the photocatalyst filter 310 be configured corresponding to the shape of the inner surface of the housing 50.

Experimental Example

A humidifier apparatus using a photocatalyst having an air-cleaning function in accordance with the present invention (example) and a humidifier apparatus having an air-cleaning function through generation of anions (comparative example) were compared.

The humidifier apparatuses of the example and the comparative example were operated for a total of 100 hours, and then were evaluated as to air-cleaning function, humidifying amount and noise generation through operation for 10 hours.

TABLE 1

|  | Air-cleaning function | Humidifying amount (g/hr) | Noise generation |
|---|---|---|---|
| Example | Excellent | about 80 g/hr | No noise |
| Comparative Example | Good (O3 (ozone) detected) | about 80 g/hr | Noise generated |

1) Air-Cleaning Function

Although both the apparatuses of the example and the comparative example provided an air-cleaning function of removing indoor toxic substances and bacteria, the apparatus of the comparative example underwent gradual reduction in generation of anions over time and generated ozone $O_3$, which is toxic to humans. On the contrary, the apparatus of the example maintained an excellent air-cleaning function over time.

2) Humidifying Amount

There was no significant difference in terms of humidifying amount between the example and the comparative example.

3) Noise Generation

The apparatus of the example generated no substantial noise in operation. On the contrary, the apparatus of the comparative example generated motor noise. There was a significant difference in terms of noise generation between the example and the comparative example when compared by an observer.

As can be seen from such an experimental example, the humidifier apparatus using a photocatalyst having an air-cleaning function according to the present invention provides excellent effects in terms of air-cleaning, humidification and noise generation, as compared with existing humidifier apparatuses having an air-cleaning function. In addition, the apparatus according to the present invention is manufactured in a column type structure, thereby providing an advantage of good space utilization.

Although some specific embodiments have been described herein with reference to the accompanying drawings, it will be understood by those skilled in the art that these embodiments are provided for illustration only, and various modifications, changes, alterations and equivalent embodiments can be made without departing from the scope of the present invention.

Therefore, the scope and sprit of the present invention should be defined only by the accompanying claims and equivalents thereof.

The invention claimed is:

1. A humidifier apparatus using a photocatalyst having an air-cleaning function, the apparatus comprising:
   a housing having
      a lower portion being received in a water tank for storing water, and
      an inlet hole for intake of external air into the housing;
   an absorption bar being disposed within the housing, and having
      a lower portion being submerged in the water, and
      a plurality of absorption pores configured to absorb the water;
   a humidifying filter
      being secured to an inner surface of the housing,
      covering an upper portion of the absorption bar, and
      having a plurality of humidifying pores configured to humidify a room, wherein the humidifying pores are combined in a first honeycomb structure;
   an adsorption filter
      being stacked on the humidifying filter, and
      having a plurality of adsorption pores configured to adsorb foreign matter introduced into the housing, wherein the adsorption pores are combined in a second honeycomb structure;
   a photocatalyst cleaning unit
      being stacked on the adsorption filter, and
      having a plurality of photocatalyst pores coated with a photocatalyst and configured to purge the foreign matter adsorbed to the adsorption filter, wherein the photocatalyst pores are combined in a third honeycomb structure; and
   a discharge unit being disposed above the photocatalyst cleaning unit, and configured to
      receive moisture from the humidifying filter and air from the housing, and
      discharge the received moisture and air to an outside of the housing, wherein a surface of the absorption bar closest to the discharge unit is coplanar with a surface of the humidifying filter closest to the discharge unit.

2. The humidifier apparatus according to claim 1, wherein the photocatalyst cleaning unit further comprises
   a light supply unit
      being disposed above the photocatalyst filter, and
      configured to emit light to the photocatalyst included in the photocatalyst filter to activate the photocatalyst.

3. The humidifier apparatus according to claim 2, wherein the light supply unit comprises:
   a light emitting unit comprising a light emitting diode (LED); and
   a power controller configured to
      operate the light emitting unit by alternating power, and
      turn on/off the light emitting unit.

4. The humidifier apparatus according to claim 1, wherein the discharge unit comprises:
   a discharge plate
      covering an upper portion of the housing, and
      having a plurality of through-holes formed therein; and
   a discharge fan
      being disposed under the discharge plate, and
      configured to
         suction air from the housing, and
         discharge the air through the discharge plate.

5. The humidifier apparatus according to claim 4, wherein the discharge unit further comprises
   a guide piece
      being connected to an upper portion of the discharge plate, and
      configured to guide a flow of the air discharged through the through-holes.

6. The humidifier apparatus according to claim 4, wherein the discharge unit further comprises
   a discharge controller configured to regulate an amount of air discharged from the housing to the outside of the housing by controlling the discharge fan.

7. The humidifier apparatus according to claim 1, wherein the housing has a cylindrical shape.

8. The humidifier apparatus according to claim 1, wherein the inlet hole is formed below the humidifying filter and above a water level of the water in the water tank.

9. The humidifier apparatus according to claim 1, wherein the adsorption pores are larger than the humidifying pores.

10. The humidifier apparatus according to claim 1, wherein the first, second, and third honeycomb structures are continuously connected with each other.

11. A humidifier apparatus using a photocatalyst having an air-cleaning function, the apparatus comprising:

a housing, wherein the housing comprises a water tank for storing water, and at least one inlet hole for intake of external air;

an absorption bar, wherein the absorption bar is partially located in the water tank, and the absorption bar comprises a plurality of absorption pores configured to absorb water;

a humidifying filter concentrically surrounding the absorption bar, wherein the humidifying filter has a plurality of humidifying pores configured receive water from the plurality of absorption pores, and a top surface of the humidifying filter is coplanar with a top surface of absorption bar;

an adsorption filter over the humidifying filter, wherein the adsorption filter has a plurality of adsorption pores configured to adsorb foreign matter;

a photocatalyst cleaning unit, wherein the photocatalyst cleaning unit has a plurality of photocatalyst pores coated with a photocatalyst and configured to purge the foreign matter adsorbed to the adsorption filter; and a discharge unit configured to discharge moisture from the humidifying filter to the external air via the adsorption filter and the photocatalyst cleaning unit.

12. The humidifier apparatus of claim 11, wherein the adsorption filter is in direct contact with the humidifying filter.

13. The humidifier apparatus of claim 11, wherein the adsorption filter is in direct contact with the absorption bar.

14. The humidifier apparatus of claim 11, wherein the adsorption filter is in direct contact with the photocatalyst cleaning unit.

15. The humidifier apparatus of claim 11, wherein the plurality of adsorption pores is a plurality of concentrically arranged adsorption pores.

16. The humidifier apparatus of claim 11, wherein the absorption bar extends from a bottom surface of the humidifying filter opposite the top surface of the humidifying filter.

* * * * *